United States Patent [19]

Ward

[11] Patent Number: 5,709,651
[45] Date of Patent: Jan. 20, 1998

[54] ADHESIVE DRESSING

[75] Inventor: William John Ward, Hull, United Kingdom

[73] Assignee: Smith & Nephew PLC, London, United Kingdom

[21] Appl. No.: 831,959

[22] Filed: Apr. 2, 1997

Related U.S. Application Data

[63] Continuation of Ser. No. 464,714, filed as PCT/GB93/02623, Dec. 22, 1993, abandoned.

[30] Foreign Application Priority Data

Dec. 24, 1992 [GB] United Kingdom ............... 9226909

[51] Int. Cl.⁶ ........................................... A61F 13/02
[52] U.S. Cl. ........................ 602/57; 602/42; 602/47; 602/58
[58] Field of Search .............. 602/41–58; 128/888, 128/889; 206/440, 441; 424/443, 445, 447, 448; D24/189

[56] References Cited

U.S. PATENT DOCUMENTS

| | | | |
|---|---|---|---|
| 4,832,008 | 5/1989 | Gilman | 602/57 |
| 5,099,832 | 3/1992 | Ward | 602/57 |
| 5,153,040 | 10/1992 | Faasse, Jr. | 428/40 |
| 5,167,613 | 12/1992 | Karami et al. | 602/58 |
| 5,489,262 | 2/1996 | Cartmell et al. | 602/57 |

FOREIGN PATENT DOCUMENTS

| | | |
|---|---|---|
| 0910800 | 10/1983 | European Pat. Off. . |
| 2224445 | 5/1990 | United Kingdom . |

*Primary Examiner*—Richard J. Apley
*Assistant Examiner*—Kim M. Lee
*Attorney, Agent, or Firm*—Larson & Taylor

[57] ABSTRACT

An adhesive dressing comprising a backing layer, a pressure sensitive adhesive thereon and a support layer attached to the non-adhesive surface of the backing layer characterized in having an additional edge strip component on the adhesive surface to aid adhesion of the dressing to the skin.

13 Claims, 1 Drawing Sheet

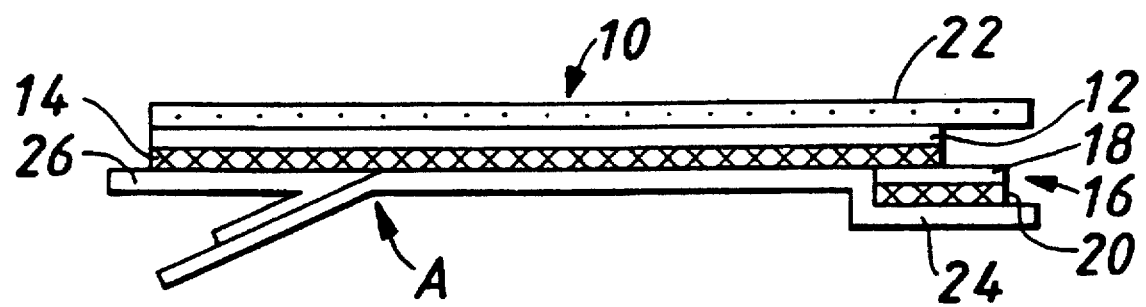

ADHESIVE DRESSING

This application is a continuation of application Ser. No. 08/464,714 filed as PCT/GB93/02623, Dec. 22, 1993, now abandoned.

FIELD OF THE INVENTION

The present invention relates to an adhesive dressing used on wound areas and in particular but not exclusively for wounds such as burns, abrasions, ulcers and surgical incisions and as a protective dressing to cover for example an indwelling catheter site and as part of an ostomy dressing for example to form the fixation for an ostomy bag.

DESCRIPTION OF PRIOR ART

There have been many different ways of presenting adhesive dressings, for example using a protector layer over the adhesive having adhesive free handles at a pair of opposed edges. Another mode of presentation as described in UK Patent No. 2224445 requires the presence of a carrier means in the form of a support layer usually of a material stiffer than the adhesive coated film adhered to the non-adhesive surface of the film and having a V-shaped handle formed from the protector. The support layer conforms to the contours of the skin to which it is applied and may be left attached to the dressing. However, it is preferred that it should be removed. Despite the fact that in such presentations the support layer extends beyond the adhesive coated film when the removal of the support layer is required it is often the case that by peeling back the support layer, the adhesive coated film will also be peeled away from its contact with skin. This is a distinct disadvantage and is often aggravated by the fact that in the first few seconds of contact of the adhesive surface of the film with the skin surface before the removal of the support layer, the adhesion at the edge of the adhesive coated film between the support layer and film is greater than that between the adhesive and the skin surface. The reduced adhesion between the film and the skin surface may be as a result of moisture on a skin surface or a body hair which interrupts the adhesive contact. This peel back effect may also be caused when the adhesive is pattern spread over a film, in which case there will be areas along the edge of the film which are not covered in adhesive and therefore will be liable to uplift with the support layer. The adhesive may also have low initial tack properties due to the adhesive being below skin temperature on contact with the skin and therefore does not show the same adhesive qualities as it does once the adhesive has been activated by body heat.

SUMMARY OF THE INVENTION

The present invention seeks to overcome the above-mentioned disadvantages by providing a novel dressing presentation which includes an additional component to aid the adhesion of the film to the skin.

According to one aspect of the present invention there is provided an adhesive dressing which comprises a conformable backing layer having a pressure sensitive adhesive layer over one surface thereof, a removable protector layer which covers the adhesive layer and extends beyond the backing layer at a contiguous edge on the backing and adhesive layers and a conformable support layer which is releasably attached to the non-adhesive surface of the backing layer and extends beyond the backing layer at said edge characterized in that attached to the adhesive layer along at least a part of said edge is a component comprising a conformable layer having a skin contacting layer of adhesive on one surface thereof, which component extends outwardly to underlie the extended portion of the conformable support layer.

According to a further aspect of the present invention there is provided a method of covering a wound and indwelling catheter or drip or any other like medical apparatus which comprises applying thereto an adhesive dressing in accordance with the invention.

According to yet a further aspect of the present invention there is provided a method of manufacture of the dressing which comprises the steps of:

casting a solution of a polymer which is to form a backing layer onto a strip of film forming a support layer spreading an adhesive onto a protector layer and laminating the adhesive and film and those associated layers together, removing the protector layer from the adhesive and, if required, trimming off a strip of film and adhesive along at least one edge of the laminate and characterized in applying a component comprising a second conformable layer, adhesive layer and protector to an edge or trimmed edge of the adhesive layer contiguous with the backing layer removing the protector layer from the component and replacing the protector layer of the adhesive dressing.

Aptly the component is applied only at the edge region.

The support layer is conformable by which is meant that the support layer will conform to the contours of a surface to which it is applied.

DESCRIPTION OF PREFERRED EMBODIMENTS

Suitably the backing layer may comprise a hydrophilic polyurethane having a water uptake of 25% such as that disclosed in example 2 of United Kingdom Patent No. 2 093 190.

Alternatively the backing layer may comprise materials which are conventionally employed to form thin film surgical dressings. Suitable materials include those described in United Kingdom Patent No. 1280631, European Patents Nos. 0051935, 0091800 and 0178740. Particularly apt materials are polyurethanes for example polyester or polyether polyurethanes known under the name ESTANE (Trade Mark) and polyether polyamides for example those known under the name PEBAX (Trade Mark). Other favoured materials include hydrophilic polymers such as hydrophilic polyurethanes including those described in United Kingdom Patent No. 2093190 especially the polyurethane described in Example 2 therein. Such materials will typically take up from 5 to 95% by weight of water.

The materials employed in the dressings of the invention may be moisture vapour permeable.

The moisture vapour transmission rate of the materials employed in the present invention may be measured by a procedure known as the Payne Cup method. The method uses a cup 1.5 cm deep with a flanged top. The inner diameter of the flange is such to provide an area for moisture vapour transmission of 10 $cm^2$. In this method 10 ml of distilled water is added to the cup and a sample of the material under test large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed as in gm-$^2$/24 hrs at 37° C. at 100% to 105 relative humidity difference. Hereinafter the units for moisture vapour transmission will be abbreviated to gm$^{-2}$.

Suitably the backing layer is moisture vapour permeable and has a moisture vapour transmission rate of at least 300 g m$^{-2}$/24 hours relative humidity difference, more suitably at least 500 g m$^{-2}$/24 hours and preferably at least 800 g m$^{-2}$/24 hours.

Suitably the backing layer has thickness of from 15 to 80 μm, more suitably 20 to 60 μm and preferably 25 to 50 μm, for example 30 μm, 35 μm and 40 μm.

The pressure sensitive adhesive layer may preferably be formed from an adhesive which is conventionally used for contact with the skin. Most desirably, the pressure sensitive adhesive is an acrylic adhesive such as an acrylate ester copolymer adhesive formed by the copolymerization of 2-ethyl-hexyl acrylate, butyl acrylate and acrylic acid. Alternatively, the adhesive layer may be an adhesive such as polyvinyl alkyl ether adhesive. Suitable adhesives are described in United Kingdom Patent No. 1280631 and European Patents Nos. 35399 and 51935.

The layer of adhesive provided on the backing layer may be a continuous layer of moisture vapor permeable adhesive such as acrylate surgical adhesives or polyvinyl ethyl ether. The moisture vapor permeable adhesive is preferably of a weight of 5 gm$^{-2}$ 50$^{-2}$ and most desirably 15 gm$^{-2}$ to 25 gm$^{-2}$.

Alternatively the layer of adhesive is a discontinuous layer of adhesive spread over the film in such a fashion as to allow moisture vapor transmission. This may be achieved by pattern spreading the adhesive whereby a regular repeated pattern of adhesive is spread over the film or may be achieved by spreading a porous adhesive. The porous adhesive may be microporous, or it may alternatively have macropores or a mixture of micro and macropores. The porous layer of adhesive allows access of skin surface moisture to the film. Favorably the diameter of the pores are 0.1 to 10 times the thickness of the adhesive layer. Suitably the pores will be from about 1000 μm in diameter.

Suitably the removable protector is a silicone coated release paper. Desirably the removable protector may be divided into two or more pieces. Preferably at least one of the protector pieces is significantly larger than the other or others and covers a major proportion of the adhesive layer. It is desirable that the stripping load of the support layer from the backing layer is equal to or greater than that of the protector from the adhesive layer otherwise there is a risk that the support layer would peel from the backing layer before the protector can be removed.

The removable protector most desirably covers and extends beyond the second conformable layer and skin contacting adhesives of the edge strip once it has been applied.

The support layer is aptly formed from a polymeric film or paper. The support layer may be attached to the backing layer by virtue of casting or extruding the backing layer onto the support layer thereby forming an attachment which is easily reversed. Most suitably the support layer maybe formed from for example, a transparent polymeric film such as a polyethylene or polypropylene film or from an opaque silicone or polyethylene coated paper.

The edge strip which comprises a conformable layer having a skin contacting layer of adhesive on one surface thereof, is preferably a continuous strip attached along the edge of the backing layer. Alternatively, the edge strip may be attached along only part of the edge of the backing layer. A further alternative may be the edge strip being attached along the edge of all of the backing layer.

The conformable layer is preferably made from the same material as the backing layer and the skin contacting layer of adhesive is also preferably that used upon the backing layer. Thus, the adhesive layer of the edge strip may be either continuous or discontinuous as described above in connection with the adhesive layer of the backing layer. Alternatively, however, the conformable layer may be made from polyvinyl ethylene or any of the alternative suggested for the backing layer. A further alternative may be materials including paper, non-woven fabric, woven fabric and films, sheets or webs of polymers including polypropylene, polyethylene, copolymers thereof and blends including polystyrene, polyester and polyvinyl chloride.

Particularly apt materials of the type mentioned above include paper, porous polyvinyl chloride sheet such as that sometimes known as PORVIC (Trade Mark) which is conventionally used in the manufacture of first aid dressings, non-woven fabric such as spun-bonded polyester fabric (SONTARA Trade Mark), polyester film (MELINEX, Trade Mark), woven acrylic fabric, embossed films of low or high density polyethylene or polypropylene, integral nets formed by the fibrillation of embossed films, and oriented polypropylene films.

The adhesive dressing may be prepared by casting a solution of the polymer which is to form the backing layer onto a long strip of the film which is to form the support layer. An adhesive layer may then be screen printed onto the protector layer. The polymer and support layer may then be laminated to the adhesive screen printed protector layer, with the cast conformable polymer layer being positioned next to the adhesive. The laminated roll may then be trimmed to the correct laminate width. The protector layer is then peeled off the adhesive, the polymerized adhesive trimmed to the final dressing width, an edge strip and a V-handle placed in position and then the protector layer replaced. The dressing may then be cut to length and placed in a bacteria proof pouch, sealed and sterilised by conventional methods including using ethylene oxide or irradiation.

To make the edge strip, cast a solution of polymer onto a strip of casting support film. Screen print the adhesive onto another protector layer and laminate the support layer and the cast conformable polymer layer to the adhesive in the same manner as above. Remove the casting support film. Trim the laminate to the desired width and apply the edge strip at the stage of the preparation of the dressing which involves removing the protector layer, ensuring that the protector layer of the edge strip is removed and replaced by the protector layer of the adhesive dressing.

BRIEF DESCRIPTION OF THE DRAWINGS

The invention will now be described strictly by way of example, with reference to the accompanying drawing which represents a diagrammatic side view of a dressing according to the invention.

The FIGURE illustrates an adhesive dressing 10 which comprises a backing layer 12 formed from a film of hydrophilic polyurethane. The backing layer 12 has upon one surface thereof a pattern spread pressure sensitive adhesive layer 14 which is formed from an acrylic adhesive. Attached to the non-adhesive surface of the backing layer 12 is a support layer 22 which supports the entire surface of backing layer 12. The support layer 22 extends beyond the backing layer 12. Attached to the adhesive layer 14 along one edge of the dressing 10 is an edge strip generally designated 16. The edge strip 16 has a conformable layer 18 which is adhered to the adhesive layer 14 and has on the remaining surface thereof a layer of skin contacting adhesive 20. The edge strip 16 extends outwardly from the backing layer 12 so as to underlie the support layer 22 which extends beyond the backing layer 12.

The adhesive layer 14 and skin contacting adhesive layer 20 are covered by a removable protector 24 and a smaller removable protector 26 also covers part of the adhesive layer 20. Both of the removable protectors 24 and 26 extend beyond the backing layer 12. The smaller removable protector 26 is folded into a V-shape and the larger removable protector 24 is essentially flat and covers both the adhesive layer 14 and adhesive layer 20 and overlaps on to the smaller cover 26 at a point indicated by the letter A.

In use the larger protector 24 is first removed and the dressing 10 held between an appliers' finger and thumb by the removable protector 26 and support layer 22. Once the area of the dressing 10 and edge strip 16 covered by the larger protector 24 is adhered to the skin, the remaining protector 26 may be removed and thus the remaining part of the dressing adhered to the skin of the patient. Immediately following this the support layer 22 is removed by holding onto and peeling back the portion of the support layer 22 which extends beyond the backing layer 12 and which the edge strip 16 underlies.

I claim:

1. An adhesive dressing comprising a conformable backing layer having a pressure sensitive adhesive layer over a first surface thereof, a removable protector which covers the adhesive layer and extends beyond the backing layer at a contiguous edge on the backing and adhesive layers and a conformable support layer which is releasably attached to a second surface of the backing layer and said conformable support layer having an extending portion which extends beyond the backing layer at said edge, a component attached to said adhesive layer along at least a part of said edge, said component comprising a conformable layer having a skin contacting layer of adhesive on one surface thereof, said component extending outwardly to underlie said extending portion of the conformable support layer and said component being attached to said adhesive layer such that said component remains in place on the adhesive dressing when the dressing is applied to the user.

2. An adhesive dressing as claimed in claim 1 wherein the backing layer is vapour permeable.

3. An adhesive dressing as claimed in claim 1 wherein the backing layer comprises polyester or polyether polyurethanes or polyether polyamides.

4. An adhesive dressing as claimed any preceding wherein the backing layer comprises a hydrophilic polyurethane having a water uptake of 5 to 95% by weight of water.

5. An adhesive dressing as claimed in claim 1 wherein the adhesive on the backing layer is a moisture vapour permeable adhesive and has a weight of 5 $gm^{-2}$ to 50 $gm^{-2}$.

6. An adhesive dressing as claimed in any preceding claim wherein the layer of adhesive on the backing layer is a discontinuous layer of adhesive spread over the film to allow moisture vapour transmission, by pattern spreading or by spreading a porous adhesive.

7. An adhesive dressing as claimed in claim 1 wherein the removable protector is divided into two or more pieces and at least one of the protector pieces is significantly larger than the other or others and covers a major proportion of the adhesive layer on the backing layer.

8. An adhesive dressing as claimed in claim 1 wherein the support layer has a stripping load from the backing layer, said stripping load being equal to or greater than that of the protector from the adhesive layer on the backing layer.

9. An adhesive dressing as claimed in claim 1 wherein the removable protector covers and extends beyond the conformable layer and skin contacting adhesive of said component.

10. An adhesive dressing as claimed in claim 1 wherein said component comprises a continuous strip attached along the edge of the backing layer.

11. An adhesive dressing as claimed in claim 1 wherein said component is attached along only part of the edge of the backing layer.

12. An adhesive dressing as claimed in claim 1 wherein said component is attached along the edge of all of the backing layer.

13. An adhesive dressing as claimed in claim 1 wherein the conformable layer of said component is made from the same material as said conformable backing layer and wherein the adhesive of the skin contacting layer of adhesive of said component is the same as the adhesive over said first surface of said conformable backing layer.

* * * * *